United States Patent [19]

Segerstad et al.

[11] Patent Number: 4,574,437
[45] Date of Patent: Mar. 11, 1986

[54] METHODS AND DEVICE FOR TERMINATING TACHYCARDIA

[75] Inventors: Christer H. A. Segerstad, Järfälla; Hans Vallin, Västerhaninge, both of Sweden

[73] Assignee: Siemens Aktiengesellschaft, Berlin and Munich, Fed. Rep. of Germany

[21] Appl. No.: 736,990

[22] Filed: May 23, 1985

Related U.S. Application Data

[63] Continuation of Ser. No. 446,673, Dec. 3, 1982, abandoned.

[30] Foreign Application Priority Data

Dec. 4, 1981 [SE] Sweden ................. 8107269

[51] Int. Cl.⁴ .............................................. A61N 1/36
[52] U.S. Cl. .............................................. 128/419 PG
[58] Field of Search .................................. 128/419 PG

[56] References Cited

U.S. PATENT DOCUMENTS

| | | |
|---|---|---|
| 3,939,844 | 2/1976 | Pequignot ................. 128/419 PG |
| 3,942,534 | 3/1976 | Allen et al. ................. 128/419 PG |
| 4,181,133 | 1/1980 | Koleniko et al. ........... 128/419 PG |
| 4,228,803 | 10/1980 | Rickards ..................... 128/419 PG |
| 4,280,502 | 7/1981 | Baker, Jr. et al. .......... 128/419 PG |
| 4,307,725 | 12/1981 | Sonton et al. .............. 128/419 PG |
| 4,406,287 | 9/1983 | Nappholz et al. .......... 128/419 PG |
| 4,408,606 | 10/1983 | Spurrell et al. ............. 128/419 PG |

Primary Examiner—William E. Kamm
Attorney, Agent, or Firm—Hill, Van Santen, Steadman & Simpson

[57] ABSTRACT

A device for terminating tachycardia emits stimulation pulses to the heart synchronized with the heartbeats and a variable time delay. In order to quickly determine the proper delay time and thus increase the chances for successfully terminating tachycardia, the device has a unit for measuring the time between successive heartbeats and for deriving a plurality of different delay times therefrom of which the shortest delay time is a selected initial value and the difference between successive delay times becomes increasingly greater. The delay times are stored in a register which may be scanned in a specific sequence.

11 Claims, 5 Drawing Figures

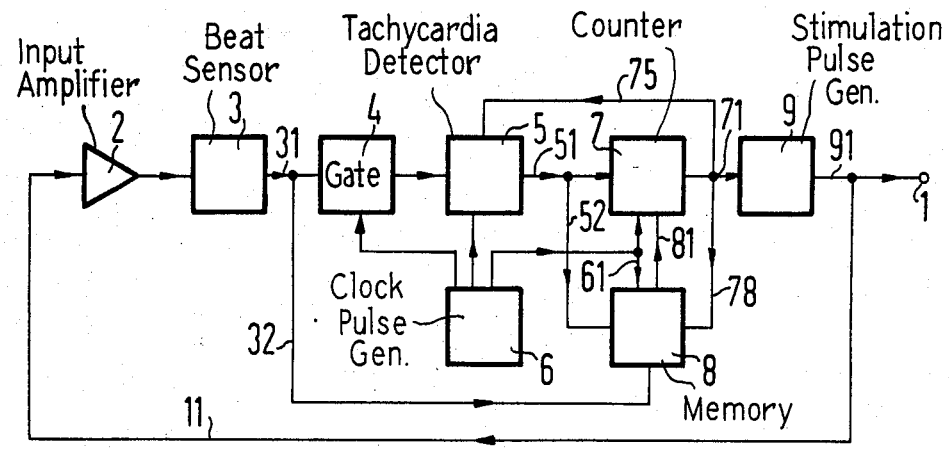
FIG. 1
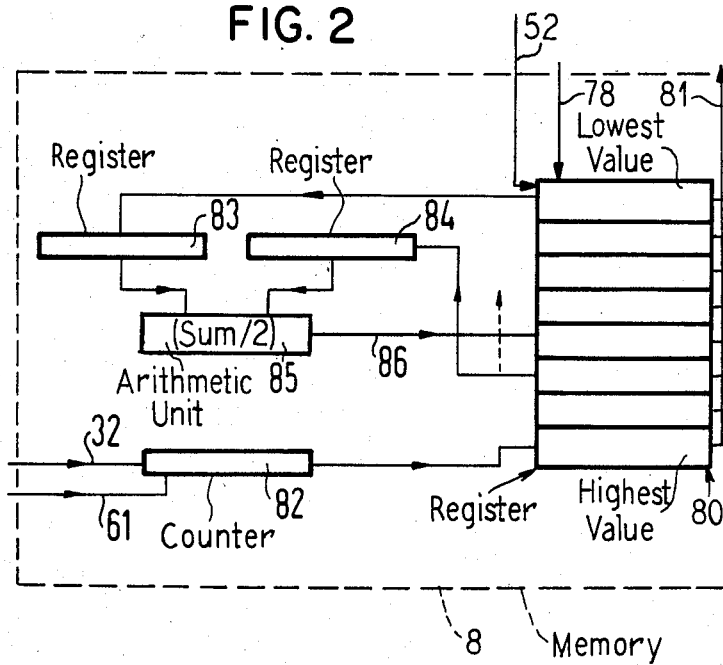
FIG. 2
FIG. 2a
| Delay ms | 1st Sequence | 2nd Sequence |
|---|---|---|
| 200 | d7 | d8 |
| 203 | d5 | d7 |
| 206 | d3 | d5 |
| 212 | d1 | d3 |
| 225 | d2 | d1 |
| 250 | d4 | d2 |
| 300 | d6 | d4 |
| 400 | d8 | d6 |

METHODS AND DEVICE FOR TERMINATING TACHYCARDIA

This is a continuation of application Ser. No. 446,673, filed Dec. 3, 1982, now abandoned.

BACKGROUND OF THE INVENTION

1. Field of the Invention

The present invention relates to methods and devices for terminating or arresting tachycardia, and specifically to such devices for emitting a stimulation pulse to the heart synchronized to heartbeats with a variable time delay which is quickly selected as the optimum delay for terminating tachycardia.

2. Description of the Prior Art

Tachycardia is the condition of an unnaturally elevated heartbeat frequency, for example, a heartbeat frequency of more than 180 beats per minute. It is known that this rapid heartbeat rhythm can be arrested by electrical stimulation pulses supplied to the heart. Such stimulation pulses must, however, be supplied to the heart within a critical time interval after a heartbeat, a so-called window. The window may be immediately after the refractory period of the heart following a heartbeat, or may be directly before a following heartbeat. It is further known that the width of the window and its location within a heartbeat cycle varies with body position, physical activities, drugs and other conditions. The windows respectively associated with such conditions or combinations of conditions may vary to such extent that the windows do not overlap, and it is therefore not possible to determine a fixed time for emitting a stimulation pulse in synchronization with the patient's heartbeat which is accurate for all conditions.

A device for terminating tachycardia having an input means responsive to heartbeat signals and a variable delay pulse circuit for supplying a stimulation pulse after a predetermined delay from one output pulse to the next by means of a feedback connection is described in U.S. Pat. No. 3,942,534. This device divides the total time interval between the termination of the refractory period and the next successive heartbeat into a grid of equidistant steps. The first stimulation pulse coincides with the end of the refractory time, the next stimulation pulse occurs, for example, ten milliseconds later, the next pulse occurs after another ten milliseconds, etc. Because the windows are frequently very narrow, the spacing between individual stimulation pulses in this conventional device must be selected correspondingly small. This, however, means that a large number of different pulses are required in order to suitably cover the entire possible interval. This results in the disadvantage that, under certain conditions, a long interval may elapse until a stimulation pulse is emitted during the critical time interval and tachycardia is arrested. Tests undertaken with devices functioning in accordance with the teachings of U.S. Pat. No. 3,942,534 have shown that under worst-case conditions, up to 15 minutes may elapse between the beginning of tachycardia and its subsequent arrest.

Further tests have shown that the ease with which tachycardia may be terminated increases as the time required to supply a stimulation pulse within the window decreases. This is particularly true for tachycardia which affect the atrioventricular node.

SUMMARY OF THE INVENTION

It is an object of the present invention to provide a device methods and for terminating tachycardia operable such that the effectively active window for terminating tachycardia in a particular patient under different conditions can be found quickly and a stimulation pulse supplied within that window to arrest the tachycardia.

The above object is inventively achieved in a device having a means for measuring the time between successive heartbeats and an arithmetic unit which derives therefrom a number of different delay times, of which the shortest delay time is a selected value and the difference between successive delay times becomes increasingly greater. The delay times are stored in a register which is scanned in a specific sequence so that the chances for supplying a stimulation pulse within the window are significantly increased, resulting in a reduction of the time required to terminate tachycardia. The device operates based upon the perception that the critical window becomes wider in direct dependence upon its position in the interval between the end of the refractory period and the following heartbeat, the window becoming wider as it occurs later in the interval. The refractory period of the heart during tachycardia is first determined in a known manner such as described, for example, in U.S. Pat. No. 4,280,502 and this value is selected as the lower limit for delay of the stimulation pulses. The device disclosed and claimed herein then determines the difference between the beat repetition time during tachycardia, and the fixed lower limiting value and subdivides the difference into a suitable number of steps (for example, 6 through 10 steps). In the simplest embodiment, the steps may be obtained by successive halving of the remaining interval. Any geometric division is possible, however, such as for example dividing the remaining interval successively into thirds. The only essential requirement is that the steps become shorter and shorter as they approach the refractory period. Independently of whether the stimulation pulses begin from the lower delay time limit or from the upper delay time limit, the total interval is covered with as few steps as possible in all instances. A suitable scanning of the interval results in the generation of a stimulation pulse after a moderate delay, followed by alternating delays on either side of the first stimulation pulse delay becoming increasingly smaller or larger. As used herein, this type of scanning is referred to as "centrifuge" scanning.

In a further embodiment of the invention, the device may include a memory for accepting different delay times. The corresponding delay times may be stored therein in a table which can be consulted in a specified pattern for delaying the successive stimulation pulses.

A further reduction in the scanning time is obtained in another embodiment of the invention wherein the delay time which successfully terminates tachycardia is entered into the memory and, upon a subsequent occurrence of tachycardia, the new search for the proper temporal position of the stimulation pulse for arresting the tachycardia is begun at the delay which successfully arrested the previous tachycardia. It is again suitable that the search for further delay times be undertaken by centrifuge scanning. Experience has shown that a substantial probability exists that even if the critical window for the renewed tachycardia is not at the same location as the window for the previous tachycardia, the new window will be disposed in close temporal proximity to the previous window. Because the stored value for terminating the earlier tachycardia is not necessarily the mean delay time value of all possible delay time values, a different number of possible steps exist in the two directions beginning at this value. During the course of centrifugally scanning all of the possible delay times, a limit may be encountered in one direction whereas many steps are still available in the other direction. In such a case, the device may, for example, successively repeat the reached limiting value until all of the steps in the other direction have been exhausted, or may directly continue searching for the proper delay time only in the one direction still exhibiting available possibilities.

In a further embodiment of the device, a plurality of stimulation pulses, rather than a single stimulation pulse, may be generated in synchronization with the heartbeats and a suitable delay, the spacing between the individual pulses comprising the plurality of pulses being a uniform value. Should, for example, tachycardia not be terminated after trying stimulation pulses emitted after the various delays, the same cycle may be repeated with a different number of stimulation pulses emitted after each delay. The variability of the device to meet widely different conditions is thus significantly increased. Not only may the delay time be varied, but also the number of respectively generated pulses after each delay can be varied, as may be spacing between such pulses in the plurality of pulses. Additionally, the sequence in which the different cycles are tried may also be selectively determined.

The different variation possibilities can be exploited in a particularly simple manner in an embodiment of the invention wherein at least a portion of the different variables and/or selectable values is programmable. A particularly simple arrangement for accomplishing this purpose embodies all of the components for the device disclosed and claimed herein, except for the input and output portions of the circuit, in a microprocessor. The tachycardia conditions, the shortest delay time (which will usually be selected slightly greater than the refractory period during tachycardia), the number of stimulation pulses which are to be generated upon the occurrence of each heartbeat (for example, 2, 3 or more, with the potential for increasing the number), and the chronological spacing between the stimulation pulses of each group of stimulation pulses may all be programmed into the microprocessor.

The device disclosed herein may also be adapted to operate either automatically at the occurrence of tachycardia, or by external activation, such as by the exterior application of a magnet. The device may also be programmed to set an upper time limit during which attempts to terminate tachycardia by stimulation pulses should continue, inasmuch as some cases of tachycardia may not be possible to terminate with the use of, or only the use of, stimulation pulses. If the device is utilized in combination with an implanted heart pacemaker, the base inhibition frequency of the heart pacemaker may also be programmed into the device. In order to assist the heart after the occurrence of tachycardia, the device may be programmed to continue to supply stimulation pulses to the heart at a normal heartbeat frequency after the tachycardia has terminated so as to urge the heart back into its proper rhythm.

The device may be entirely or partially accommodated in a known manner in an external device, as described in European patent application No. 79301539.7 in connection with a different device, operating in co-operation with an implanted heart pacemaker for driving the heart pacemaker during tachycardia.

DESCRIPTION OF THE DRAWINGS

FIG. 1 is a schematic block diagram of a device for terminating tachycardia constructed in accordance with the principles of the present invention.

FIG. 2 is a detailed schematic block diagram of the memory shown in the device in FIG. 1.

FIG. 2a is a table showing exemplary computed delay times and two sequences with which the delay times may be scanned.

DESCRIPTION OF THE PREFERRED EMBODIMENTS

Figure 3:
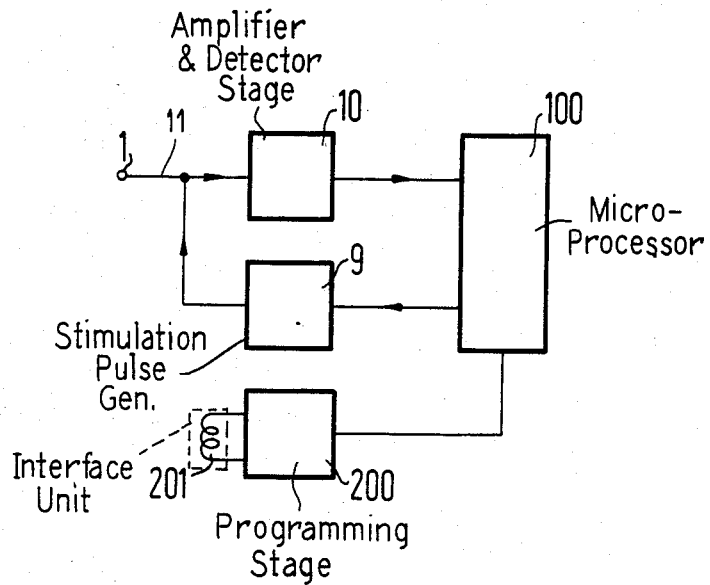
FIG. 3 is a schematic block diagram of a second simplified embodiment of the device shown in FIG. 1.

A device for terminating or arresting tachycardia is shown in FIG. 1. The device has a terminal 1 for connection to an electrode leading to the heart. Pulses may be supplied to the heart via the terminal 1 and the electrode connected thereto, and the heart activity, specifically heartbeats, can also be sensed via this terminal. Heartbeats are supplied from the terminal 1 to an input amplifier 2 via a line 11. The output of the amplifier 2 is supplied to a beat sensor 3, which responds only to heartbeats. The output signals from the beat sensor are supplied via a line 31 and a gate 4 to a tachycardia detector 5, which may be a computer. The gate 4 is controlled by a clock pulse generator 6 so as to permit transfer of output signals from the beat sensor 3 to the tachycardia detector 5 only during a specific time interval, for example, 2 seconds. When the number of pulses proceeding to the tachycardia detector 5 reaches or exceeds a predetermined value within this time interval, tachycardia is assumed to exist and the tachycardia detector 5 generates an output signal enabling a counter 7 via a line 51 and a memory 8 via a line 52.

The memory 8 has an internal arithmetic unit shown in greater detail in FIG. 2. A specific value for a delay time for a stimulation pulse is supplied by the memory 8 to the counter 7. The counter 7 additionally receives clock pulses from the clock pulse generator 6 at a frequency of, for example, 1 kHz. The output signal of the counter 7 is forwarded over a line 71 to a stimulation pulse generator 9 which emits a stimulation pulse or a group of stimulation pulses via a line 91 to the terminal 1 corresponding to the signal received from the counter 7. The output signal of the counter 7 is additionally forwarded via a line 75 to the tachycardia detector 5 as a reset signal. The output of the counter 7 is also connected over a line 78 to the memory 8 for controlling a change in the delay time value subsequently forwarded from the memory 8 to the counter 7. The memory 8 is continuously supplied with the high frequency clock signal from the clock pulse generator 6. The output signal of the beat sensor 3 is also supplied to the memory 8 via a line 32.

Figure 4:
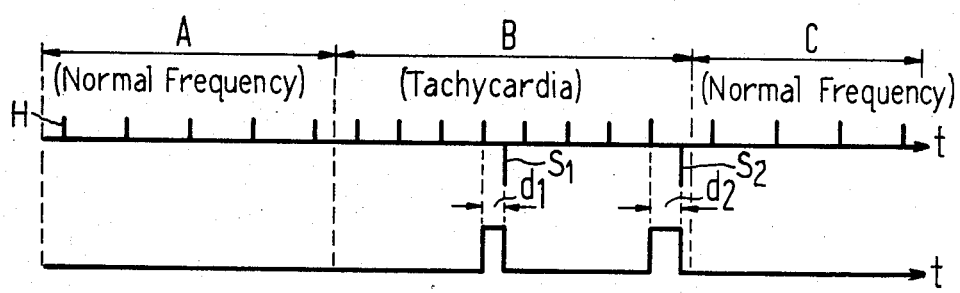
FIG. 4 is a pulse diagram illustrating the manner of operation of the device shown in FIG. 1.

The manner of operation of the device shown in FIG. 1 is explained below with the aid of the pulse diagrams shown with respect to time t in FIG. 4. The sequence of events shown in FIG. 4 begins with a period A of normal frequency of heartbeats H, the heartbeat frequency being, for example, less than 150 beats per minute. Under such conditions, the number of signals corresponding to heartbeats supplied to the tachycardia detector 5 during the interval in which the gate 4 is open does not reach the threshold value necessary to trigger an output signal from the tachycardia detector 5. Thus no stimulation pulses are generated, as evidenced by the absence of pulses in the bottom graph shown in FIG. 4.

In the following period B, tachycardia is assumed to occur, as evidenced by an increase in the frequency of heartbeats H. The tachycardia detector 5 thus forwards an output signal for enabling the counter 7 and the memory 8. The counter 7 counts backward from a delay time value $d_1$, transferred from the memory 8 to the counter 7, utilizing the clock frequency from the clock pulse generator 6 until reaching zero and subsequently emits an output signal driving the stimulation pulse generator 9 for generating a stimulation pulse. The delay time is shown in the bottom graph of FIG. 4 as a rectangular pulse. A first stimulation pulse $S_1$ is shown in FIG. 4 as a negative pulse emitted at the end of the delay time $d_1$. In the present example, it is assumed that the stimulation pulse $S_1$ is not at the proper temporal distance from the preceding heartbeat in order to terminate tachycardia. After a renewed occurrence of the prescribed number of tachycardia heartbeats (four such heartbeats in the example of FIG. 4) the tachycardia detector 5 again begins the delayed generation of a stimulation pulse, however, with an increased delay time $d_2$. It is now assumed that the stimulation pulse $S_2$ emitted after this delay time terminates tachycardia. In period C of FIG. 4, the heart has again returned to its normal heart rhythm.

As schematically shown in FIG. 1, whenever the counter 7 drives the stimulation pulse generator 9, the tachycardia detector 5 is simultaneously reset to its starting point, and further a signal is forwarded to the memory 8 on the basis of which a different delay time value is supplied to the counter 7. When tachycardia is terminated after this delay time, that is, when no output signal is supplied by the tachycardia detector 5 at the end of a prescribed time, the contents of the memory 8 are shifted in the opposite direction by means of a signal on line 52 so that the counter 7 again receives the earlier delay time value. The device is thus "reminded" of the proper delay time value which successfully terminated tachycardia. Upon a renewed occurrence of tachycardia, the first-emitted stimulation pulse is emitted to the heart with the same time delay as was successfully employed previously.

One embodiment of the memory 8 is shown in greater detail in FIG. 2. The memory 8 includes a register 80 having, in the example shown in FIG. 2, eight address locations. The smallest possible time delay is, for example, permanently entered into the uppermost address. This time delay either corresponds to the refractory period or is slightly greater than the refractory period. The largest possible time delay is entered into the lowest address, this time delay corresponding to the interval between two tachycardia heartbeats. This time is determined, for example, by a counter 82 to which clock pulses from the clock generator 6 are supplied via the line 61 and to which heartbeat signals are supplied via the line 32. The number of clock pulses arising between two successive heartbeats is utilized to measure the elapsed time in that interval. The smallest value for a delay time is entered in a register 83, and the greatest value for a delay time is entered in a register 84. An arithmetic unit 85 computes half of the sum of these two values and transmits the result via a line 86 to the next address of the register 80. This value is then inscribed in the register 84 as an updated value, and the arithmetic operation is again undertaken, the result being entered in the register 80 at the next address. This process is repeated until all addresses of the register 80 are occupied.

In the example shown in FIG. 2, it is assumed that the interval between successive tachycardia heartbeats is 400 milliseconds and that the refractory period of the heart (and thus the shortest delay time) is 200 milliseconds. The delay times $d_1$ through $d_8$ computed based on these assumptions are shown in tabular form in FIG. 2a. The sequence column in the table shown in FIG. 2a illustrates the sequence with which the delay times $d_1$ through $d_8$ are supplied to the counter 7 when the interval between successive tachycardia heartbeats is centrifugally scanned. The delay time $d_1 = 212$ milliseconds is first supplied to the computer 7, followed by the second delay time $d_2 = 225$ milliseconds, followed by the third delay time $d_3 = 206$ milliseconds, and so on. Because, in the example shown in FIG. 4, the second delay time $d_2$ resulted in a successful termination of tachycardia, this value represents the first delay time which will be utilized upon a renewed occurrence of tachycardia. A further embodiment of the device is shown in FIG. 3. As in FIG. 1, the device has a terminal 1 for connection to an electrode leading to the heart. Signals from the terminal 1 proceed via a line 11 to an amplifier and detector stage 10 which combines the operations of amplifying the signal and detecting tachycardia. Output signals from the stage 10 are supplied to a microprocessor 100 which identifies and determines the various intervals and conducts the necessary arithmetic operations for generating the delay times. The output of the microprocessor 100 controls a stimulation pulse generator 9 for supplying stimulation pulses to the heart via the terminal 1 and the electrode connected thereto.

As further shown in FIG. 3, the microprocessor 100 may be programmed by means of a programming stage 200 connected to an interface unit 201. A similar programming means may also be provided in the embodiment shown in FIG. 1.

Both of the embodiments shown in FIG. 1 and FIG. 3 may be used in combination with an implanted heart pacemaker which emits stimulation pulses to the heart in the event of other instances of heart arrhythmia.

The above illustrations have been described for the purpose of generating a single stimulation pulse after the proper delay time is found, however, as also discussed above, a group of stimulation pulses may be supplied after the proper delay time with specific prescribed temporal distances between the pulses in the group.

Although other modifications and changes may be suggested by those skilled in the art, it is the intention of the inventors to embody within the patent warranted hereon all changes and modifications as reasonably and properly come within the scope of their contribution to the art.

We claim as our invention:

1. A device for terminating tachycardia in a heart comprising:
    a detector means for detecting tachycardia and for generating an output signal upon the detection thereof;
    a measuring means for measuring the interval between successive tachycardia heartbeats;

a delay generating means connected to said detector means and said measuring means, said delay generating means having an arithmetic means for deriving a plurality of different delay times from said interval, a shortest of said delay times being at least equal to the refractory period of said heart and successively derived delay times being increasingly longer by increasingly longer amounts, and having a counter means for determining said refractory period and a scanner means for scanning said delay times beginning with said shortest period; and an output means connected to said counter means for generating at least one stimulation pulse for supply to said heart at the end of each scanned delay time.

2. The device of claim 1 wherein said arithmetic means derives said plurality of different delay times by successively halving the difference between said interval and each preceding delay time and adding said difference to said shortest delay time.

3. The device of claim 1 further comprising a memory for storing said plurality of different delay times at respective addresses in a sequence for scanning of said address sequence by said scanner means.

4. The device of claim 3 wherein said counter-means centrifugally scans said memory.

5. The device of claim 3 wherein said detector means includes means for generating a signal after passage of a selected period during which no tachycardia is detected by said detector means thereby indicating successful termination of tachycardia by a last-scanned delay and said memory having means for shifting said address sequence upon receipt of said signal for bringing said last-scanned delay to an address which will be first scanned by said scanner means upon a renewed occurrence of tachycardia.

6. The device of claim 1 wherein said output circuit generates a plurality of said stimulation pulses at the end of each scanned delay time, the pulses in said plurality of stimulation pulses being at uniformly spaced temporal distances.

7. The device of claim 6 wherein, if said scanner means completes a delay time scanning cycle and tachycardia is not terminated, said scanner means continues a further scanning cycle of said delay times and further comprising means for supplying a signal from said counter means to said output circuit if tachycardia is not terminated for varying the number of stimulation pulses generated at the end of each scanned delay time.

8. The device of claim 6 wherein, if said scanner means completes a delay time scanning cycle and tachycardia is not terminated, said scanner means continues a further scanning cycle of said delay times and further comprising means for supplying a signal from said counter means to said output circuit if tachycardia is not terminated for varying said uniform temporal distances between said pulses in said plurality of stimulation pulses.

9. The device of claim 1 further comprising a time means for generating specified time intervals and a gate means disposed between said means and said heart and connected to said timer means for permitting heartbeat information to be supplied to said detector means only during said specified time intervals.

10. A method for terminating tachycardia in a patient comprising the steps of:

monitoring the heartbeats of the patient to detect tachycardia;

selecting a shortest delay time which is at least equal to the refractory period of the patient's heart;

deriving a plurality of increasingly longer delay times from said shortest delay time which differ in succession by increasingly longer amounts;

storing said delay times in a selected sequence in sequential addresses of a memory; and if tachycardia is detected, scanning said sequential addresses and supplying a stimulation pulse to the heart following periodic heartbeats, said stimulation pulse being delayed by differently increasingly longer delay times from said sequence until tachycardia is terminated.

11. A method for terminating tachycardia as claimed in claim 10 comprising the additional step of:

shifting said sequential addresses in said memory after tachycardia is terminated such that the delay time which successfully terminated tachycardia is stored in an address which will be first scanned upon a renewed occurrence of tachycardia.

* * * * *